United States Patent [19]

Rahn et al.

[11] Patent Number: 4,624,573

[45] Date of Patent: Nov. 25, 1986

[54] TOTAL OPTICAL LOSS MEASUREMENT DEVICE

[76] Inventors: John P. Rahn, 22420 Gilmore, Canoga Park, Calif. 91307; C. Denton Marrs, 414 Ashworth, Ridgecrest, Calif. 93555

[21] Appl. No.: 609,942

[22] Filed: May 14, 1984

[51] Int. Cl.⁴ .......................................... G01N 21/55
[52] U.S. Cl. .................................. 356/445; 356/239; 356/432; 356/448
[58] Field of Search .............................. 356/445–448, 356/371, 244, 124–128, 237, 239, 359–360, 369, 32–35.5, 349, 432

[56] References Cited

U.S. PATENT DOCUMENTS

| | | | |
|---|---|---|---|
| 3,499,716 | 3/1970 | Bennett | 356/445 |
| 3,761,179 | 9/1973 | Plummer et al. | 356/371 |
| 3,796,495 | 3/1974 | Laub | 356/359 X |
| 3,930,732 | 1/1976 | Holly | 356/349 X |
| 3,947,127 | 3/1976 | Bennett et al. | 356/124 |
| 3,999,865 | 12/1976 | Milam et al. | 356/239 |
| 4,156,571 | 5/1979 | Ljung | 356/445 |
| 4,269,518 | 5/1981 | Rahn | 356/445 |
| 4,339,199 | 7/1982 | Jones et al. | 356/360 X |
| 4,353,650 | 10/1982 | Sommargren | 356/371 |
| 4,480,916 | 11/1984 | Bareket et al. | 356/360 X |
| 4,571,085 | 2/1986 | Anderson | 356/445 |

FOREIGN PATENT DOCUMENTS 0154443 12/1980 Japan .................................. 356/446

OTHER PUBLICATIONS

Virgil Sanders, "High-Precision Reflectivity Measurement Technique for Low-Loss Laser Mirrors", *Applied Optics*, vol. 16, No. 1, Jan. 1977, pp. 19 and 20.

Herbelin et al., "Development of Laser Mirrors of Very High Reflectivity Using the Cavity-Attenuated Phase-Shift Method", *Applied Optics*, vol. 20, No. 19, 10-1-81, pp. 3341-3344.

*Primary Examiner*—Davis L. Willis
*Attorney, Agent, or Firm*—W. Thom Skeer

[57] ABSTRACT

The total optical loss caused by laser induced damage to an optical component is measured by monitoring the phase shift during mirror reflectance or transmission. The phase shift is directly proportional to the amount of loss. A secondary laser illuminates the area under test with a coherent light beam well below the component's damage threshold. This reference beam is modulated. The reflected or transmitted reference beam is monitored by a photomultiplier tube whose output is fed to a lock-in circuit. The lock-in circuit compares the phase of the received light to the induced modulation.

6 Claims, 2 Drawing Figures

TOTAL OPTICAL LOSS MEASUREMENT DEVICE

BACKGROUND OF THE INVENTION

1. Field of the Invention

This invention pertains to a device that measures the optical loss at a specific location on a mirror surface or at a specific location on a lens surface. In particular, it pertains to a device for measuring the degradation of optical loss in real-time by the amount of phase shift in coherent light. This loss is the fractional reduction in optical power which occurs upon reflection of light from the mirror surface.

2. Description of the Prior Art

Previously, each optical characteristic of a sample mirror has been measured separately on a different system. Reflectance, absorption, transmission and scatter have each required separate evaluation techniques. These quantities could be combined for the total optical loss of a sample mirror. In particular, total optical loss was measured as a composite of these characteristics and if a total optical loss system was evaluated, there was no way to measure changes in total optical loss caused by strong or damaging illumination of the surface. Thus, whether the individual characteristics were being measured or an overall figure of merit was being determined, the individual characteristics of a sample mirror were not determined as a function of induced damage. Measurements simply identified before and after characteristics.

SUMMARY OF THE INVENTION

A limited area of a sample mirror or lens within a resonant cavity is evaluated for total optical loss. Evaluation of total optical loss in each section of a large mirror or lens permits an overall figure of merit to be determined for large optical components. The evaluation of the total optical loss also permits measurements of the change in optical loss as damage is induced at the point of measurement. A test laser provides a low level illumination of the area to be evaluated. This illumination is well below the damage threshold and is modulated in a predetermined manner. A damaging laser with appropriate focusing optics is then directed to the same area and damage is commenced by illuminating with the damaging laser past the damage threshold levels. A photomultiplier tube is used to observe the output from the resonant cavity of the test laser system and its modulated light. The modulation of the test laser system is controlled by a signal generator. The signal generator and the output of the photomultiplier tube are input to a lock-in amplifier which compares the phase of the modulated illumination to the output illumination. Any other state-of-the-art monitoring means such as an oscilloscope or other monitoring device may also be used to compare the output intensity and phase shift with respect to the input intensity and phase shift. For an ideal situation with no loss, there would be an infinite phase shift.

DETAILED DESCRIPTION OF THE INVENTION

Figure 1:
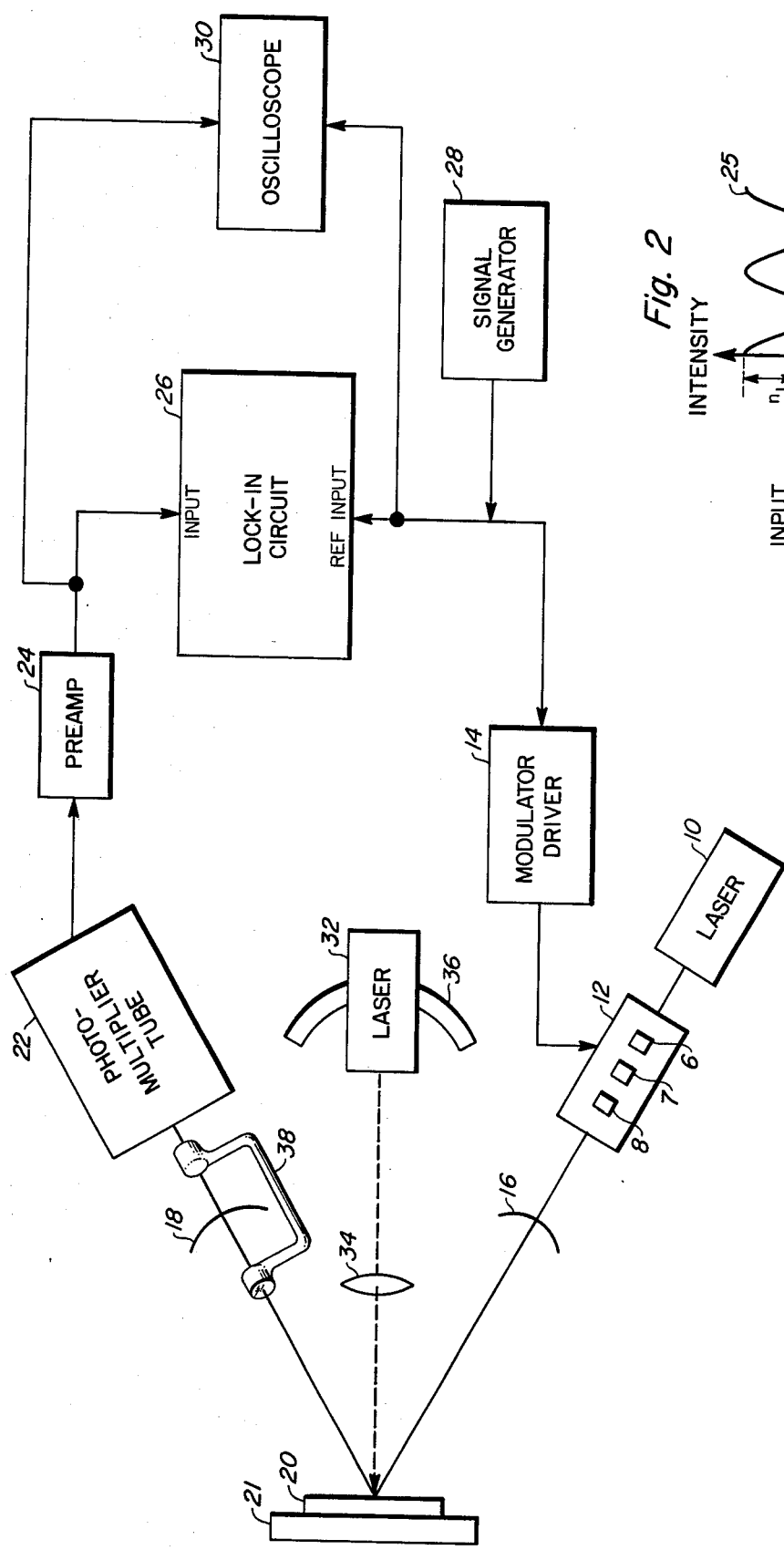
FIG. 1 is a block diagram of the present invention.

FIG. 1 is a block diagram of the present invention for testing of mirrors. For testing of lenses, the transmittance requires the exit mirror to be behind the sample. A test laser system 10 emits a coherent light beam. The phrase laser system means that all elements of a necessary coherent light emission system are present. For a typical laser this includes resonant cavity, active media, flash tube, entrance and exit mirrors. Test laser system 10 has an output intensity well below the damage threshold of a sample which is to be evaluated. A modulator 12 is used to vary the output intensity from test laser system 10. Modulator 12 is driven by a modulator driver 14. Modulator 12 may be two Pockels cells 6 and 8 with a polarizer 7 between them. Pockels cells 6 and 8 are rotated such that by reversing the voltage across them they produce opposite phase shifts of equal magnitude. First Pockels cell 6 and polarizer 7 produce amplitude and phase modulation. Second Pockels cell 8 demodulates the phase leaving only amplitude modulation. Both modulator 12's components and modulator driver 14 are standard optical devices commercially available. The modulated beam passes through an entrance mirror 16 which is one end of a resonance cavity whose second end is defined by an exit mirror 18. A sample mirror 20, which has a surface to be tested, is placed in the resonance cavity to form a fold. If a transmissive optic, such as a lens or antireflection coating, is to be tested exit mirror 18 is behind sample 20 so that the path extends oppositely from the sample and no fold occurs. A fold in the resonance cavity means that light traveling along a path reflects off the mirror and either back along itself or back in a different direction. Sample mirror 20 is mounted in a two-axis mount 21 which permits sample mirror 20 to be translated within a plane. This permits all sections of its surface to be used at the same place in the resonant cavity. In this case, light traveling between entrance mirror 16 and exit mirror 18 via reflection from sample mirror 20 will follow a resonant path. The total loss for a round trip in the resonant cavity is equal to the loss for the entrance mirror 16 and the exit mirror 18 plus twice the loss of the sample mirror 20 because light reflects from the sample mirror twice in one round trip. The output from this resonant cavity is monitored by a photomultiplier tube 22. Photomultiplier tube 22 is placed in line with light passing through exit mirror 18. The overall length of a resonant cavity is defined as L. Photomultiplier tube 22 has a preamp 24 connected to its output to serve as a signal amplifier or signal conditioner. Preamp 24's output is fed to a lock-in circuit 26 which is driven by a signal generator 28. Signal generator 28 is also the signal source for modulator driver 14. Thus, signal generator 28 serves to synchronize lock-in circuit 26. The synchronization permits lock-in circuit 26 to compare the initial amplitude and phase of light from modulator 12 with the arrival amplitude and phase of light at photomultiplier tube 22. For purposes of example, signal generator 28 provides a sinusoidal modulation shown as input on FIG. 2.

Figure 2:
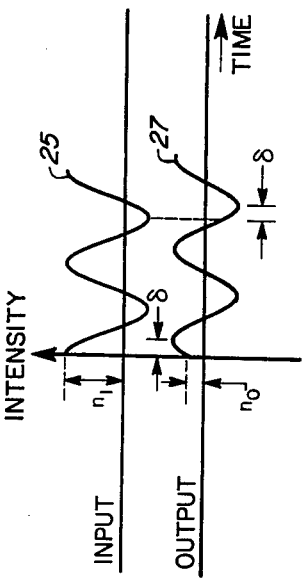
FIG. 2 is a graphic illustration of the difference between input and output intensity of the test laser signal.

In FIG. 2, input signal 25 is compared to output signal 27 which is adjusted to allow for the brief time delay in light traveling from modulator 12 to photomultiplier tube 22. The maximum amplitude $H_o$ of the output beam is reduced with respect to the maximum input amplitude $H_i$. The phase shift of peaks by an amount $\delta$ is due to the total optical loss during reflection off the sample mirror. As the sample mirror undergoes damage, both the reduction in amplitude and phase shift will change.

A monitoring means such as oscilloscope 30 or other reference devices connected to signal generator 28 and preamp 24 to observe the real-time signal. Lock-in circuit 26 measures amplitude and phase of the reference signal to the output after total optical loss. The total optical loss appears as a reduced amplitude and as a phase shift. Lock-in 26 records the input and output intensity versus time similar to that shown in FIG. 2.

Phase is measured by nulling out the signal. This forces the reference frequency to be in quadrature with the output signal so the difference in phase is measured. If there is no loss, there is no phase shift. The loss is defined by the equation $l=2L/c\delta t$ where l = round trip fractional loss for whole resonator;
2L = round trip, which is the resonator cavity length doubled;
c = speed of light;
$\delta$ = phase difference in radians between input and output modulated light power; and
t = period of modulation.

Test laser system 10 can be any laser which is subject to reasonable modulation, approximately 10 microseconds for 100 KHz. If the sample being tested does not have high loss, modulation at higher frequencies than 100 KHz will gain more sensitivity.

Sample mirror 20 is subject to destructive testing by a damaging laser 32. Damaging laser 32 is a laser system capable of output above the damage threshold of sample mirror 20. Damaging laser 32 is on a mount 36 which provides a path for shifting the angle of incidence for light from damaging laser 32. This permits damage due to different angles of incidence to be determined. Varying the angle of incidence may have significant changes in varying the destructive illumination. The angle of incidence may also be changed by pivoting the resonant cavity. Focusing optics 34 are placed in the path of light from damaging laser 32 to control the focus and illumination on sample mirror 20. The area illuminated by test laser system 10 will coincide with the focus spot for focusing optics 34. A periscope 38 of known total loss permits input to be measured by photomultiplier tube 22 without resonance between entrance mirror 16 and exit mirror 18. Periscope 38 is emplaced as shown in FIG. 1 to calibrate photomultiplier tube 22 and adjust lock-in circuit 26. Periscope 38 is moveably mounted about said exit mirror to direct light to tube 22 without resonating in the cavity and is removed to permit actual operation.

This permits a very small portion of a mirror to be evaluated for total loss due to reflectance, absorption, transmission, and scatter. The change in the total loss of the test sample during damage is measured in real time. This during lifetime measurement permits monitoring of the rate of change of total loss for a given type of mirror. By shifting the mirror in the reflection plane the entire surface can be evaluated for good and bad portions and to produce an overall figure of merit.

It is obvious to those skilled in the art that numerous modifications to the above may be made.

What is claimed is:

1. A device for measurement of optical loss of an optical element; the device comprising:
   an optically resonant cavity defined by an entrance mirror and an exit mirror and having a predetermined optical path therebetween;
   means for mounting the sample optical element within said cavity and in said path;
   means for emitting a beam of coherent light modulated with a predetermined input signal into the cavity through the input mirror and along said path;
   monitoring means, which receives said beam after exit from the cavity through the exit mirror, for generating an output signal corresponding to the modulation of said beam after such optical loss at the sample element;
   measureement means for comparing said output signal with said input signal to evaluate said optical loss; and periscope means at
   the exit mirror for directing light to said monitor means without resonance between the entrance mirror and the exit mirror, the periscope means being removable for resonant operation of the cavity and being emplaceable therein to receive said beam along said path between the sample element and the exit mirror and to bypass the beam around the exit mirror and to said monitor means for calibration of said monitor means and said measureemnt means.

2. A device for measurement of optical loss of an optical element, the device comprising:
   an optically resonant cavity defined by an entrance mirror and an exit mirror and having a predetermined optical path therebetween;
   means for mounting the sample optical element within said cavity and in said path;
   means for emitting a beam of coherent light modulated with a predetermined input signal into the cavity through the input mirror and along said path so that said beam illuminates a predetermined area of the sample element;
   means, which receives said beam after exit from the cavity through the exit mirror, for generating an output signal corresponding to the modulation of said beam after such optical loss at the loss at the sample element;
   measurement means for comparing said output signal with said input signal to evaluate said optical loss;
   damaging means for outputting and for focussing laser light onto said predetermined area so as to induce damage of the element thereat, said damage changing said loss for evaluation thereof by said measurement means; and
   periscope means at the exit mirror for directing light to said monitor means without resonance between between the entrance mirror and the exit mirror, the periscope means being removable for resonant operation of the cavity and being emplaceable therein to receive said beam along said path between the sample element and the exit mirror and to bypass the beam around the exit mirror and to said monitor means for calibration of said monitor means and said measurement means.

3. A device for measurement of optical loss of an optical element; the device comprising:
   an optically resonant cavity defined by an entrance mirror and an exit mirror and having a predetermined optical path therebetween;
   means for mounting the sample optical element within said cavity and in said path;
   means for emitting a beam of coherent light modulated with a predetermined input signal into the cavity through the input mirror and along said path;

monitor means, which receives said beam after exit from the cavity through the exit mirror, for generating an output signal corresponding to the modulation of said beam after such optical loss at the sample element;

measurement means for comparing said output signal with said input signal to evaluate said optical loss; and periscope means to exit mirror for directing light to said monitor means without resonance between the entrance mirror and the exit mirror, the periscope means being removeable for resonant operation of the cavity and being emplaceable therein to receive said beam along said path between the sample element and the exit mirror and to bypass the beam around the exit mirror and to said monitor means for calibration of said monitor means and said measurement means.

4. The device of claim 3 wherein the sample element is reflective and folds said path.

5. The device of claim 3 wherein the sample element is transmissive and said path extends oppositely therefrom.

6. The device of claim 3 wherein said beam illuminates a predetermined area of the sample element, and wherein the device further comprises damaging means for outputting and for focussing laser light onto said predetermined area so as to induce damage of the element thereat, said damage changing said loss for evaluation thereof by said measurement means.

* * * * *